(12) United States Patent
You et al.

(10) Patent No.: US 10,773,016 B2
(45) Date of Patent: Sep. 15, 2020

(54) IMPLANTABLE MICRO BUBBLE PUMP FOR DRUG DELIVERY AND BIOMEDICAL APPLICATIONS

(71) Applicants: Lydia G You, Alexandria, VA (US); Michael C You, Alexandria, VA (US); Liangzhi You, Alexandria, VA (US)

(72) Inventors: Lydia G You, Alexandria, VA (US); Michael C You, Alexandria, VA (US); Liangzhi You, Alexandria, VA (US)

(*) Notice: Subject to any disclaimer, the term of this patent is extended or adjusted under 35 U.S.C. 154(b) by 315 days.

(21) Appl. No.: 15/859,621

(22) Filed: Dec. 31, 2017

(65) Prior Publication Data
US 2019/0201615 A1 Jul. 4, 2019

(51) Int. Cl.
| A61M 5/00 | (2006.01) |
| A61M 5/142 | (2006.01) |
| A61M 5/145 | (2006.01) |
| A61M 5/168 | (2006.01) |
| A61M 37/00 | (2006.01) |
| A61M 31/00 | (2006.01) |

(52) U.S. Cl.
CPC ........ *A61M 5/14276* (2013.01); *A61M 5/145* (2013.01); *A61M 5/14216* (2013.01); *A61M 5/168* (2013.01); *A61M 5/16877* (2013.01); *A61M 37/0015* (2013.01); *A61M 5/16827* (2013.01); *A61M 31/002* (2013.01); *A61M 2037/0023* (2013.01)

(58) Field of Classification Search
CPC .......... A61M 5/14276; A61M 5/14216; A61M 5/145; A61M 5/168; A61M 5/16877; A61M 37/0015; A61M 5/16827; A61M 31/002; A61M 2037/0023
See application file for complete search history.

(56) References Cited

U.S. PATENT DOCUMENTS

| 3,787,884 A | 1/1974 | Demer |
| 4,596,575 A * | 6/1986 | Rosenberg ........ A61M 5/14276 128/DIG. 12 |
| 4,938,742 A | 7/1990 | Smits |
| 6,283,718 B1 | 9/2001 | Prosperetti |
| 2016/0231223 A1* | 8/2016 | Wang ................. G01N 15/1404 |
| 2018/0104408 A1* | 4/2018 | Li ......................... A61M 5/158 |

* cited by examiner

*Primary Examiner* — Steven O Douglas

(57) ABSTRACT

A micro bubble pump comprises a narrow tube with two liquid columns separated by a gas bubble. Separate reservoirs containing respective fluids are connected to either of the liquid columns through small valve-controlled openings. External ultrasound waves imposed on the liquid columns oscillate the bubble, allowing it to shrink and expand and causing liquid to flow into and out of the tube respectively. In a preferred embodiment, the inlet and outlet valves are replaced with diffusers. The micro bubble pump has no moving parts and can be actuated by remote energy sources.

20 Claims, 9 Drawing Sheets

IMPLANTABLE MICRO BUBBLE PUMP FOR DRUG DELIVERY AND BIOMEDICAL APPLICATIONS

FIELD OF THE INVENTION

The present invention generally relates to a liquid pump and, more particularly, to a liquid pump which utilizes a pulsating bubble as actuator to transport liquid through channels of micro-devices.

BACKGROUND OF THE INVENTION

Micro-pumps, generally defined as handling fluid volume on the order of 1 milliliter and below, have wide applications in chemical, biological and medical systems, particularly related to precision medicine in the past decades. Among the first micro-pumps, Smits (Reference [1]) used them in controlled insulin delivery systems for maintaining diabetics' blood sugar levels without frequent needle injections. Recently, micro-pumps are used to dispense engineered macromolecules into tumors or the bloodstream to destroy cancer cells. The most well-known application of micro-pumps might be the ink-jet printheads developed in the 1970s by IBM (Reference [2]), which are still widely used today. A micro scale chamber made from piezoelectric material are made to contract by the application of an electric charge. As the chamber contracts, ink contained in it is forced out through the nozzle as a droplet. As the chamber returns to its original state, capillary action causes ink to flow into the chamber from the ink supply, making it ready to produce the next drop.

Micro-pumps, or pumps in general, are divided into two major categories: displacement pumps, which exert pressure on the working fluid through moving boundaries, and dynamic pumps, which continuously add energy to the working fluid. Smits' insulin delivery pump and the ink-jet printhead belong to the first category, while the common centrifugal pumps, and the latest eletrohydodynamic pumps are in the second one.

There are some major drawbacks of the existing micro-pumps. The major one is the complexity of the actuation mechanism and the micro-valves. These micro-pumps are hard to fabricate in micro scale and they have moving parts which are subject to mechanical failure, wearing, stress and fatigue. Such delicate parts also prevent their true miniaturization. For example, piezoelectric micro-pump could not be made less than the size of its piezoelectric disks which is around 10 mm. Reliability, power consumption, cost and biocompatibility are the critical factors in developing implantable micro-pumps. The deficiencies in these areas have precluded widespread implantation of micro-pumps.

Recent developments in the microfluidic market has drawn out more and more new micro-pump designs from both industry and academia. Micro bubble pumps are among the fastest developing categories. One type of micro bubble pump is the thermal-bubble-actuated micro-pump, which is based on thermopneumatic actuation. Prosperetti's micro-pump (Reference [3]) consists of a resistive heater arranged in a conical-shaped chamber connecting two liquid reservoirs. The actuation mechanism comes from periodically nucleating and collapsing thermal bubbles within the conical-shaped chamber. Zimmermann et al. (Reference [4]) designed a planar micro-pump which could be easily integrated into micro systems. This micro-pump comprises of heat resistors for generation of vapor bubbles and two in-plane flap valves for flow control. Similarly, cyclic pulsing of the resistive heaters causes bubbles to grow and collapse in the bubble chamber, which provides the pumping action. Although thermal bubbles can be easily generated even if the pump is small, heat loss and residual bubbles can decrease the flow rate significantly.

Besides thermal-bubble-actuated micro-pumps, micro bubble pumps utilizing electrochemical energy have also been developed. Kabata et al. (Reference [5]) proposed a prototype micro-pump for insulin administration. Hydrogen bubbles are generated through electrolysis of water in a closed chamber when electric current is present in the water, exerting pressure on the insulin solution through a silicone rubber diaphragm separating the two liquids. In Kabata's design, electric current is produced through oxidation of a silver anode. The electrochemically driven microwell drug delivery device reported by Chung et al. (Reference [6]) applies a similar mechanism. Instead of oxidizing silver anode, Chung et al.'s device produces an electric current by dissolution of a gold membrane. For this type of micro bubble pump, no external energy supply is needed and the chemical reactions provide fast drug delivery. However, actuation based on electrochemical energy has issues in the continuous supply of materials and their compatibility with microfluidics or in vivo environments.

Recently, micro-propulsion of oscillating bubbles through excitation of external acoustic waves has drawn the attention of many scientists as an alternative actuation mechanism. The advantage of acoustic energy is that it can act on the bubble remotely from an outside source so that the micro-pump does not need internal energy to function. This feature is critically important in biomedical applications and drug delivery as it is non-invasive and greatly simplifies the design of the bubble pump. Dijkink et al. (Reference [7]) built an acoustic bubble propulsion device called the "acoustic scallop", consisting of a small tube immersed in liquid and closed at one end with a bubble trapped inside. The bubble oscillations generate a quasi-steady streaming flow that eventually produces propulsion forces in the device. Feng et al. (Reference [8]) reported a micro-propulsion-based underwater micros-swimmer for navigating microfluidic environments and possibly narrow passages in the human body to perform drug delivery and other tasks.

The present invention aims an implantable, non-invasive, compact and biocompatible device for drug delivery and biomedical applications.

REFERENCES

[1] Smits, J. G. (1990) Piezoelectric micropump with microvalves, U.S. Pat. No. 4,938,742 A

[2] Demer, F. M. (1974) Ink jet printer, U.S. Pat. No. 3,787,884

[3] Prosperetti, A., et al. (2001) Bubble based micropump, U.S. Pat. No. 6,283,718 B1

[4] Zimmermann, S., Frank, J. A., Liepmann, D. and Pisano, A. P. (2004) A planer micropump utilizing thermo-pneumatic actuation and in-plane flap valves, Proc. 17th IEEE Int. Conf. on Micro Electro Mechanical Systems, (Maastricht, The Netherlands)

[5] Kabata, A., Okamura, K., Suzuki, H., Kishigami, Y, Kikuchi, M., and Haga, M. (2008) Prototype micropump for insulin administration based on electrochemical bubble formation, J. Pharm. Sci., 97(11), pp. 5037-5045

[6] Chung, A. J., Huh, Y. S., Erickson, D. (2009) A robust, electrochemically driven microwell drug delivery system for controlled vasopressin release, Biomed Microdevices, 11, pp. 861-867

[7] Dijkink, R. J., van der Dennen, J. P., Ohl, C. D., and Prosperetti, A. (2006) The 'acoustic scallop': a bubble-powered actuator, J. Micromech. Microeng, 16, pp. 1653-1659

[8] Feng, J., Yuan, J. and Cho, S. K. (2015) Micropropulsion by an acoustic bubble for navigating microfluidic spaces, Lab Chip, 15, pp. 1554-1562

SUMMARY OF THE INVENTION

The present invention is directed to a device of a micro bubble pump utilizing a pulsating bubble as the actuator and corresponding method for using the micro bubble pump for transporting liquid. The device comprises a narrow tube with two liquid columns separated by a gas bubble. Separate reservoirs containing respective fluids are connected to either of the liquid columns through small valve-controlled openings. External ultrasound waves oscillate the bubble, allowing it to shrink and expand and causing liquid to flow into and out of the tube respectively. In a preferred embodiment, the inlet and outlet valves are replaced with diffusers. The micro bubble pump has no moving parts and can be operated without physical connection or electric wiring to the device, ideal for such applications as an implantable device for drug delivery and biomedical applications.

BRIEF DESCRIPTION OF THE DRAWINGS

The foregoing and other objects, aspects and advantages will be better understood from the following detailed description of a preferred embodiment of the invention with reference to the drawings.

FIG. 1 (b) shows operation of a two-sided two-reservoir micro bubble pump during a discharge stroke.

FIG. 2 (b) shows a design with one common reservoir connected to the two inlet valves and a common mixing chamber connected to the two outlet valves during discharge stroke.

FIG. 3 (b) shows operation of a one-sided micro bubble pump during discharge stroke.

FIG. 4 (b) shows an alternative design by replacing the inlet and outlet valves with diffusers during discharge stroke.

DETAILED DESCRIPTION OF THE INVENTION

The present invention is directed to a micro-pump for pumping liquids, and more specifically to a micro bubble pump that transports liquids from a liquid reservoir to a liquid chamber by using pulsating gas bubbles as actuators without any moving mechanical parts.

When a gaseous bubble in liquid is excited by acoustic waves, its shape undergoes periodical oscillations. The bubble volume expansion and compression displace the liquid surrounding the bubble. Described here is a novel implementation of this concept and its potential use in microfluidics and medicine.

Figure 1:
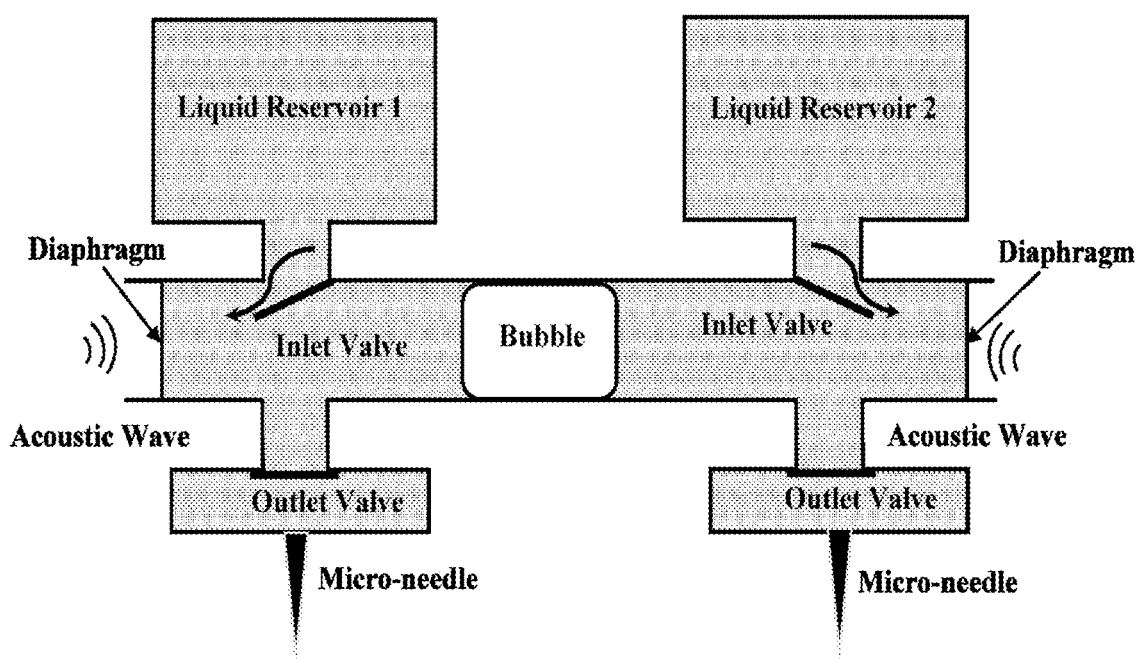
FIG. 1 (a) shows operation of a two-sided two-reservoir micro bubble pump during an intake stroke.
Figure 1:
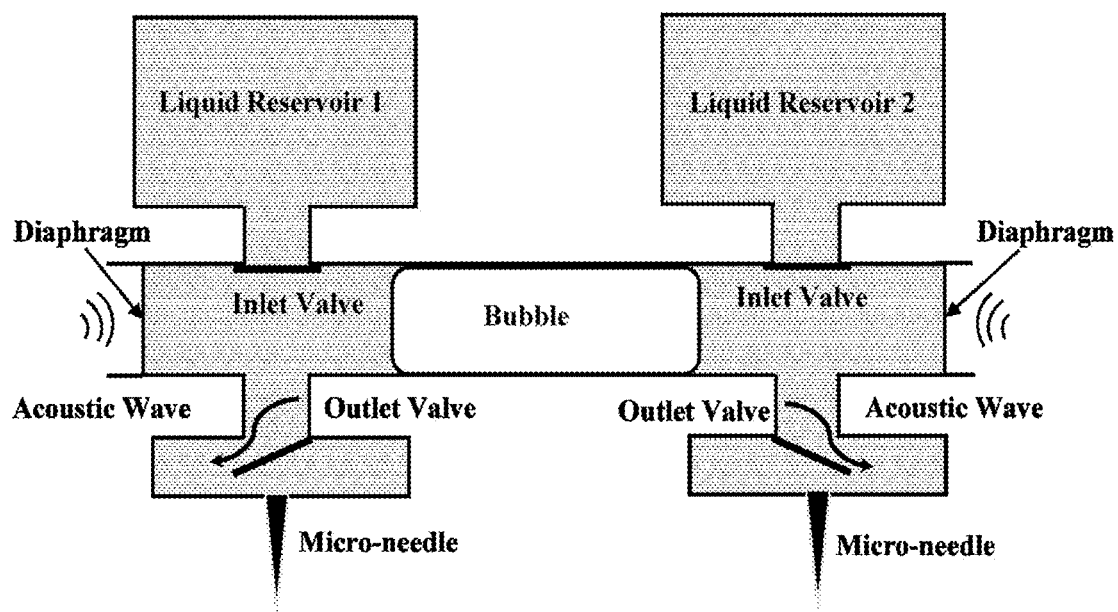

FIG. 1 shows an embodiment of the present invention. A micro-pump consists of a small tube enclosed by diaphragms at both ends, with a gas bubble located at the middle and occupying the whole cross-section of the tube, and two liquid columns at the two ends. The cross-section can be circular shape or non-circular shape. Two liquid reservoirs, connected to the tube, lie on either side of the bubble. Two outlet chambers are connected in a similar fashion to the tube. FIG. 1 (a) shows operation of the device in liquid intake stroke corresponding to bubble compression mode. When the bubble shrinks under the force of external acoustic waves from both sides, the inlet valves open and liquid flows into the tube from the liquid reservoirs. FIG. 1 (b) shows operation of the device in liquid discharge stroke corresponding to bubble expansion mode. In liquid discharge stroke, when bubble expands, the inlet valves close and the outlet valves open, squeezing liquid into the respective liquid outlet chambers which are respectively connected to respective micro-needles or other means for injecting. Under the periodical motion of the acoustic waves, the bubble pump undergoes continuous intake-discharge cycles pumping liquid from the liquid reservoirs to outlet chambers. Note the liquids in the two reservoirs are not necessarily the same type. The two-sided design is especially advantageous in a situation that requires two different liquids be transported at the same time.

Figure 2:
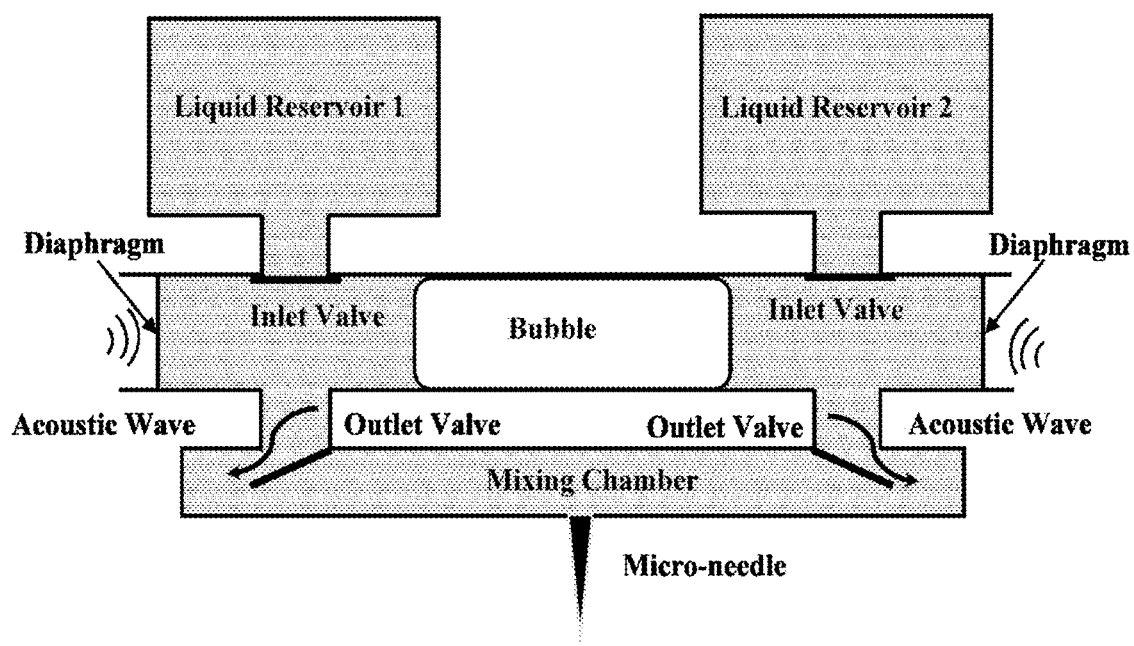
FIG. 2 (a) shows a design with two separate reservoirs connected to the two inlet valves respectively and a common mixing chamber connected to the two outlet valves during discharge stroke.
Figure 2:
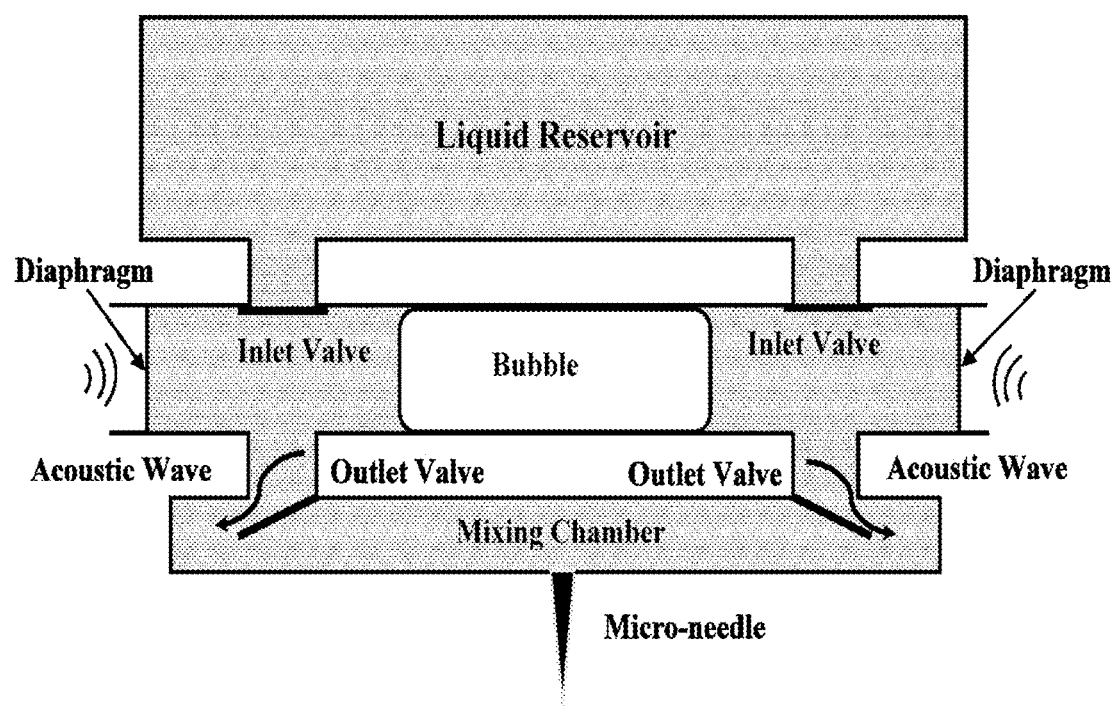

FIG. 2 (a) shows another embodiment of the present invention. In this embodiment, the device has two separate liquid reservoirs as shown in FIG. 1, but has only one common outlet chamber. FIG. 2 (a) shows the operation of this embodiment in liquid discharge stroke corresponding to bubble expansion mode. The liquid intake stroke corresponding to bubble compression mode in this embodiment is similar to the embodiment shown in FIG. 1 (a). Similarly, when bubble shrinks under the force of external acoustic waves from both sides, the two inlet valves open and liquid flows into the tube from the two liquid reservoirs. The liquid discharge stroke corresponding to bubble expansion mode is slightly different. When bubble expands under external acoustic waves, the two inlet valves close and the two outlet valves open, pushing liquid into the one common outlet chamber connected to a micro-needle or other means for injecting. This design is especially advantageous in a situation that requires mixing two different liquids immediately prior to injection or pre-mixing of liquids are not preferred.

FIG. 2 (b) shows another embodiment of the present invention. In this embodiment, the device has one common outlet chamber as shown in FIG. 2 (a), and also has only one common liquid reservoir. FIG. 2 (b) shows the operation of this embodiment in liquid discharge stroke corresponding to bubble expansion mode. The liquid discharge stroke corresponding to bubble expansion mode is similar to the embodiment shown in FIG. 2 (a). Similarly, when bubble expands under external acoustic waves, the two inlet valves close and the two outlet valves open, pushing liquid into the one common outlet chamber connected to a micro-needle or other means for injecting. The liquid intake stroke corresponding to bubble compression mode is slightly different. When bubble shrinks under external acoustic waves, the two outlet valves close and the two inlet valves open, sucking liquid into the tube from the common liquid reservoir. This design is intended for use in a situation when a single liquid is present and higher flow rate is desired.

Figure 3:
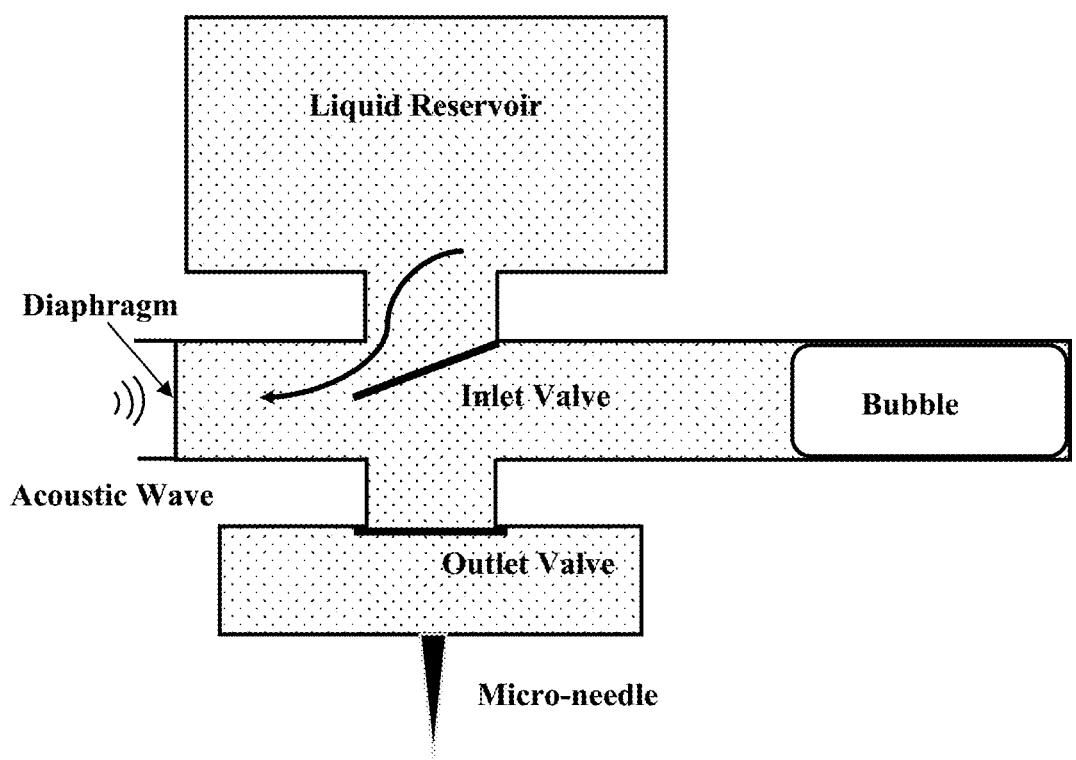
FIG. 3 (a) shows operation of a one-sided micro bubble pump during an intake stroke.
Figure 3:
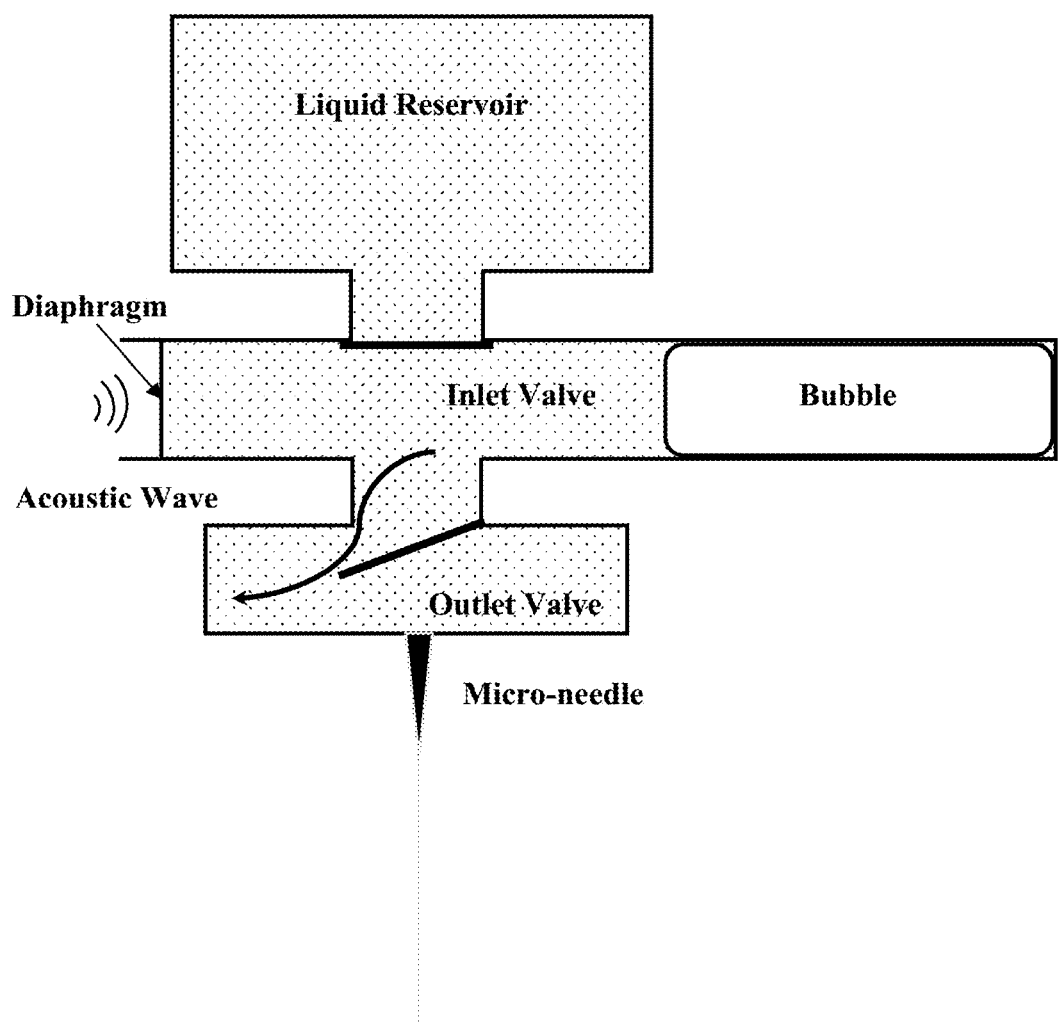

For an implantable micro-pump, compactness is a critical factor influencing the comfort of the patient. In order to reduce the overall size, a further embodiment is disclosed with only one half the size of the above mentioned two-sided micro-pumps. This one-sided micro bubble pump has a tube closed at one end and connected to a separation diaphragm at the other end. The device has a bubble located near the closed end and a liquid column filling the space between the bubble and the diaphragm. The operation principle for the one-sided pump is similar to that of the two-sided pump and is illustrated in FIGS. 3 (a) and 3 (b). FIG. 3 (a) shows operation of the device in liquid intake stroke corresponding to bubble compression mode. When the bubble shrinks under the force of external acoustic waves from one side, the inlet valve opens and liquid flows into the tube from the liquid reservoir. FIG. 3 (b) shows operation of the device in liquid discharge stroke corresponding to bubble expansion mode. In liquid discharge stroke, when bubble expands, the inlet valve close and the outlet valve open, squeezing liquid into the liquid outlet chamber which is connected to a micro-needle or other means for injecting.

Figure 4:
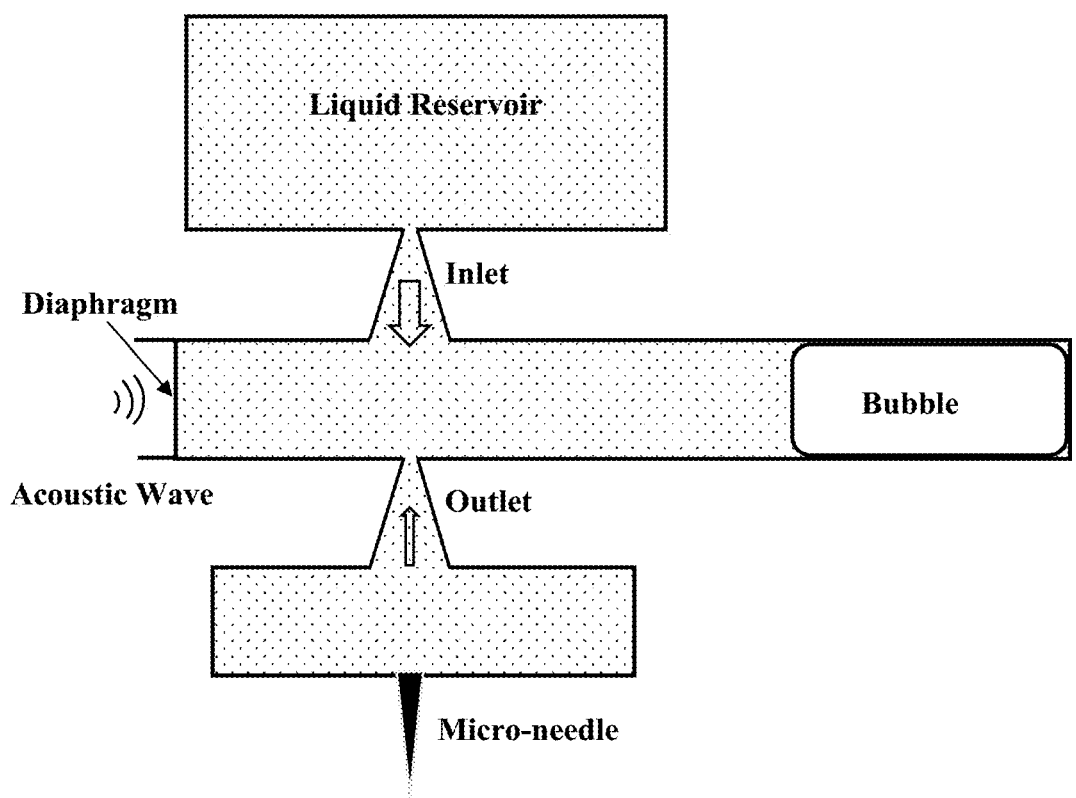
FIG. 4 (a) shows an alternative design by replacing the inlet and outlet valves with diffusers during intake stroke.
Figure 4:
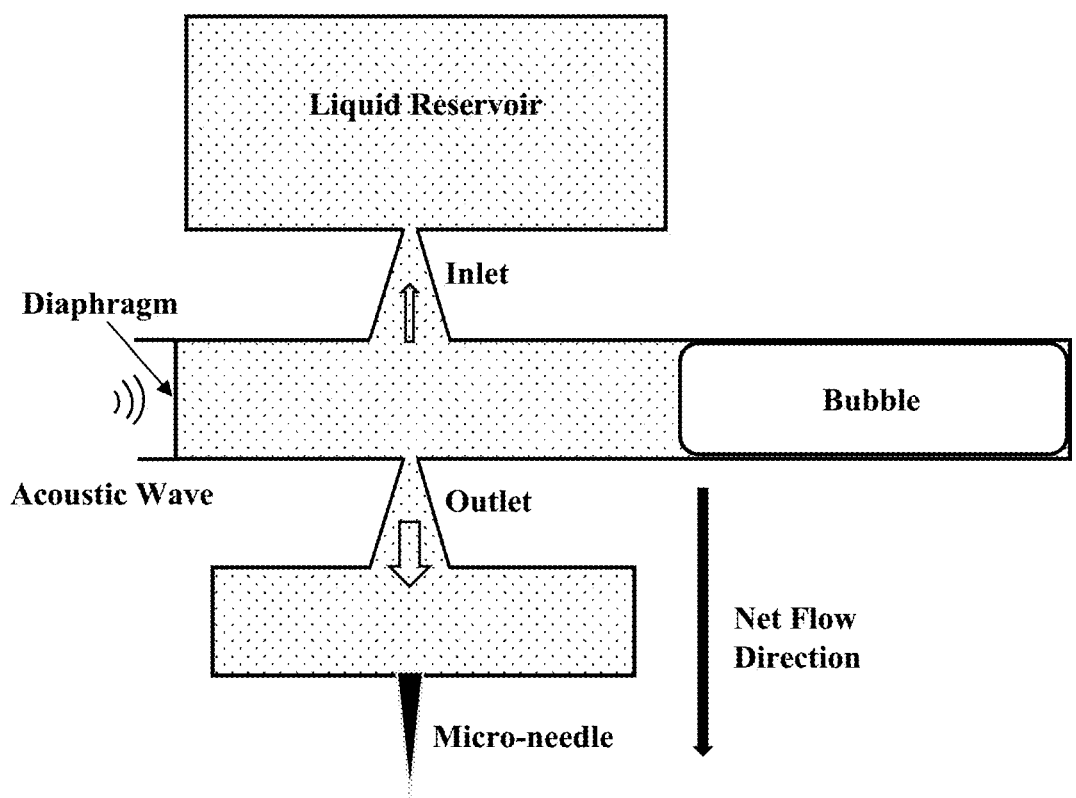

In the above embodiments micro valves (inlet and outlet valves) are used to control the intake and discharge of liquids into and from the tube. Micro valves generally increase the complexity of the fabrication process and the possibility of clogging the pathways of the microfluidic, especially when the size of the system decreases. Further the existence of valves influences the flow rate. Therefore it is highly desirable to design valve-less micro-pumps. In a preferred embodiment of the present invention, micro diffusers are used to replace the micro valves. FIG. 4 shows an exemplary embodiment. The overall design is similar to the design shown in FIG. 3, but with the inlet and outlet valves replaced with diffusers. FIG. 4 (a) shows operation of the device in liquid intake stroke corresponding to bubble compression mode. When the bubble shrinks under the force of external acoustic waves from one side, the negative pressure in the tube extracts liquids from both the liquid reservoir and outlet chamber into the tube. Due to the special configuaration of the diffusers (conical shape) and the arrangement of the two the diffusers (the larger diameter side of the inlet diffuser is connected to the tube and the smaller diameter side of the outlet diffuser is connected to the tube), the liquid volume flowing into the tube through the inlet diffuser (illustrated using a wider arrow) is larger than the liquid volume flowing into the tube through the outlet diffuser (illustrated using a narrower arrow). Therefore there exists a net flow entering the tube. FIG. 4 (b) shows operation of the device in liquid discharge stroke corresponding to bubble expansion mode. Conversely, when the bubble expands under the force of external acoustic waves from one side, the positive pressure in the tube pushes the liquid to exit the diffusers. Due to the special configuration and arrangement of the two diffusers, the liquid volume exiting through the inlet diffuser (illustrated using a narrower arrow) is smaller than the liquid volume exiting through the outlet diffuser (illustrated using a wider arrow). Therefore there exists a net flow entering the outlet chamber. Under the periodical motion of the acoustic waves, the bubble pump undergoes continuous intake-discharge cycles pumping liquid from liquid reservoir to outlet chamber.

The present invention is not limited to the above embodiments. For example, more than one bubbles can be used as actuators and accordingly more than two liquid reservoirs and/or outlet chambers can be implemented.

In considering the performance of the bubble pump, the system's behavior near resonance frequency is of the most interest since it determines the efficiency of the bubble pump. The natural frequency of a spherical bubble in unbound liquid is inversely proportional to the bubble's radius as given by Minnaert frequency $$f_0 = \frac{1}{2\pi a}\sqrt{\frac{3\gamma P_A}{\rho}},$$

where a is the radius of the bubble, γ is the polytropic coefficient, $P_A$ is the ambient pressure, and ρ is the density of the liquid. For a bubble confined in a tube by a tube wall and liquid columns and driven by external acoustic waves as disclosed in present embodiments, its natural frequency is determined not only by the dimensions of the system (lengths of the bubble and the liquid columns, tube cross-section dimensions), the polytropic coefficient, the ambient pressure, and the density of liquid, but also by the external driving frequencies of the acoustic waves.

Figure 5:
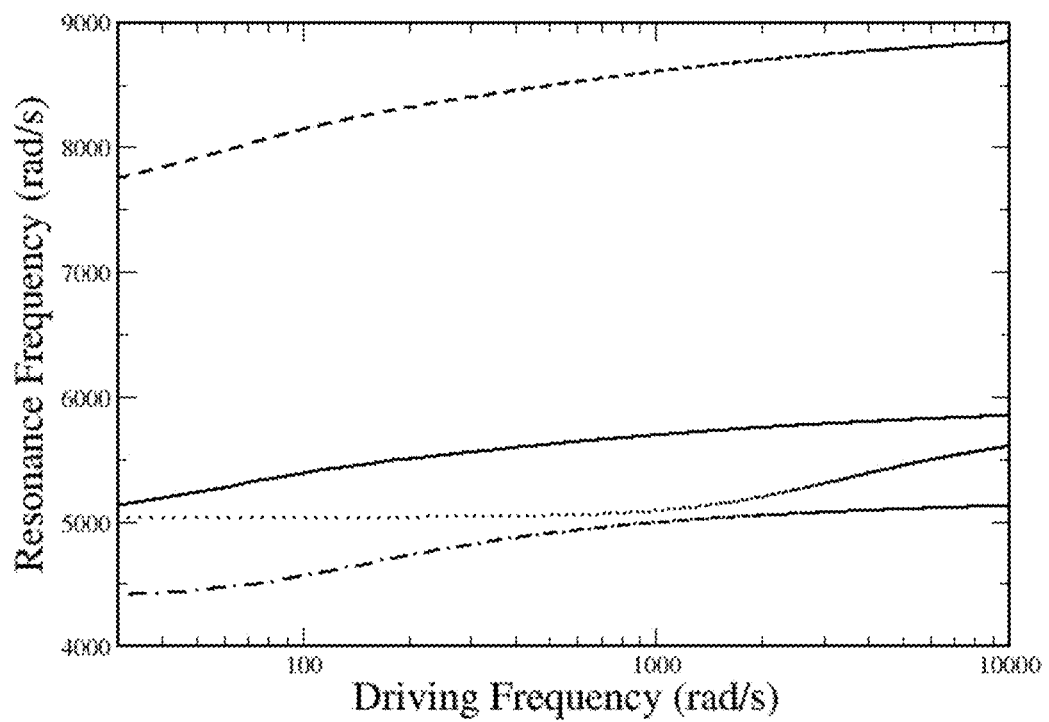
FIG. 5 shows resonance frequency of the gas-liquid system as a function of external driving frequency.

FIG. 5 shows resonance frequency of the system as a function of external driving frequency using mathematical modeling. In the calculation it is assumed that the tube is round and the tube length is 10 mm (this includes the length of the bubble and the lengths of the two liquid columns). For larger tubes (radius=1 mm), the resonance frequency increases as driving frequency increases (solid line, dash-dotted line and dash line). For smaller tubes (radius=0.2 mm), the resonance frequency as function of driving frequency is nearly constant when the driving frequency is low, and increases as driving frequency increases when the driving frequency is high (dotted line). This is because when driving frequency is low, isothermal behavior prevails for small gas bubbles. For situations when the bubble is located at the center of the tube (the two liquid columns having equal lengths), the curves are relatively close to each other (solid line, dotted line and dash-dotted line). However, when the bubble is located off the center of the tube, the resonance frequencies (dash line) have remarkable increases relative to the symmetrical cases. Placing the bubble at the center of the tube results in a minimum resonance frequency when the total liquid column length keeps unchanged.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

The invention claimed is:

1. A micro-pump for pumping liquids between containers, comprising:
    a tube, the tube filled with a gas bubble and two liquid columns, the gas bubble being located at a middle portion of the tube and the two liquid columns being located respectively at the two sides of the gas bubble, the tube being covered with diaphragms at two ends;
    a first liquid reservoir connected to the tube through a first inlet valve;
    a second liquid reservoir connected to the tube through a second inlet valve;
    a first liquid chamber connected to the tube through a first outlet valve;
    a second liquid chamber connected to the tube through a second outlet valve; and external acoustic wave supplier for driving the bubble into periodic oscillations, wherein when the bubble compresses, the first inlet valve and the second inlet valve open, and the first outlet valve and the second outlet valve close; and wherein when the bubble expands, the first inlet valve and the second inlet valve close, and the first outlet valve and the second outlet valve open.

2. The micro-pump of claim 1, wherein the first liquid reservoir and first liquid chamber are located in the same side of the bubble, and the second liquid reservoir and second liquid chamber are located in the other side of the bubble.

3. The micro-pump of claim 2, wherein the first liquid reservoir and the first liquid chamber contain a first type of liquid, and the second liquid reservoir and the second liquid chamber contain a second type of liquid.

4. The micro-pump of claim 3, wherein the first type of liquid is the same as the second type of liquid.

5. The micro-pump of claim 3, wherein the first type of liquid is different from the second type of liquid.

6. The micro-pump of claim 4, wherein the first liquid chamber and the second liquid chamber are further combined to form a common liquid chamber.

7. The micro-pump of claim 5, wherein the first liquid chamber and the second liquid chamber are further combined to form a common liquid chamber.

8. The micro-pump of claim 1, wherein the first liquid reservoir and second liquid reservoir are combined to form a common liquid reservoir.

9. The micro-pump of claim 1, wherein the first liquid chamber and the second liquid chamber are combined to form a common liquid chamber.

10. The micro-pump of claim 1,
wherein the first inlet valve, the second inlet valve, the first outlet valve, and the second outlet valve are replaced with a first inlet diffuser, a second inlet diffuser, a first outlet diffuser, and a second outlet diffuser respectively; and
wherein the first inlet diffuser, the second inlet diffuser, the first outlet diffuser, and the second outlet diffuser are conical shaped, each having a larger diameter end and a smaller diameter end.

11. The micro-pump of claim 10, wherein the larger diameter end of the first inlet diffuser is connected to the tube, the smaller diameter end of the first inlet diffuser is connected to the first liquid reservoir; the larger diameter end of the second inlet diffuser is connected to the tube, the smaller diameter end of the second inlet diffuser is connected to the second liquid reservoir; the smaller diameter end of the first outlet diffuser is connected to the tube, the larger diameter end of the first outlet diffuser is connected to the first liquid chamber; the smaller diameter end of the second outlet diffuser is connected to the tube, and the larger diameter end of the second outlet diffuser is connected to the second liquid chamber.

12. A micro-pump for pumping liquid between containers, comprising:
a tube, having a first end and a second end, the tube filled with a gas bubble and a liquid column, the gas bubble being located at the first end of the tube which is closed, the liquid column occupying the rest of the tube, and the second end of the tube being covered with a diaphragm;
a liquid reservoir connected to the tube through an inlet valve;

a liquid chamber connected to the tube through an outlet valve; and external acoustic wave supplier for driving the bubble into periodic oscillations, wherein when the bubble compresses, the inlet valve opens, and the outlet valve closes; and wherein when the bubble expands, the inlet valve closes, and the outlet valve opens.

13. The micro-pump of claim 12, wherein the inlet valve and the outlet valve are replaced with an inlet diffuser and an outlet diffuser respectively, and wherein the inlet diffuser and the outlet diffuser are conical shaped, each having a larger diameter end and a smaller diameter end.

14. The micro-pump of claim 13, wherein the larger diameter end of the inlet diffuser is connected to the tube, the smaller diameter end of the inlet diffuser is connected to the liquid reservoir, the smaller diameter end of the outlet diffuser is connected to the tube, and the larger diameter end of the outlet diffuser is connected to the liquid chamber.

15. A method for pumping liquids between containers of a micro-pump, comprising:
providing a tube, the tube filled with a gas bubble and two liquid columns, the gas bubble being located at a middle portion of the tube and the two liquid columns being located at the two sides of the gas bubble, the tube being covered with diaphragms at two ends;
providing a first liquid reservoir connected to the tube through a first inlet valve;
providing a second liquid reservoir connected to the tube through a second inlet valve;
providing a first liquid chamber connected to the tube through a first outlet valve;
providing a second liquid chamber connected to the tube through a second outlet valve; and
applying external acoustic waves on the diaphragms at the two ends of the tube and generating periodic bubble oscillations,
wherein when the bubble compresses, the first inlet valve and the second inlet valve open, and the first outlet valve and the second outlet valve close; and
wherein when the bubble expands, the first inlet valve and the second inlet valve close, and the first outlet valve and the second outlet valve open.

16. The method of claim 15, further comprising:
providing a first type of liquid in the first liquid reservoir, and a second type of liquid in the second liquid reservoir, the first type and the second type being different types.

17. The method of claim 15, further comprising:
replacing the first inlet valve, the second inlet valve, the first outlet valve, and the second outlet valve with a first inlet diffuser, a second inlet diffuser, a first outlet diffuser, and a second outlet diffuser respectively,
wherein the first inlet diffuser, the second inlet diffuser, the first outlet diffuser, and the second outlet diffuser are conical shaped, each having a larger diameter end and a smaller diameter end.

18. The method of claim 17, wherein the larger diameter end of the first inlet diffuser is connected to the tube, the smaller diameter end of the first inlet diffuser is connected to the first liquid reservoir; the larger diameter end of the second inlet diffuser is connected to the tube, the smaller diameter end of the second inlet diffuser is connected to the second liquid reservoir; the smaller diameter end of the first outlet diffuser is connected to the tube, the larger diameter end of the first outlet diffuser is connected to the first liquid chamber; the smaller diameter end of the second outlet diffuser is connected to the tube, and the larger diameter end of the second outlet diffuser is connected to the second liquid chamber.

19. A method for pumping liquid between containers of a micro-pump, comprising:
   providing a tube, having a first end and a second end, the tube filled with a gas bubble and a liquid column, the gas bubble being located at the first end of the tube which is closed, the liquid column occupying the rest of the tube, and the second end of the tube being covered with a diaphragm;
   providing a liquid reservoir connected to the tube through an inlet valve;
   providing a liquid chamber connected to the tube through an outlet valve; and
   applying external acoustic waves on the diaphragm at the second end of the tube and generating periodic bubble oscillations,
   wherein when the bubble compresses, the inlet valve opens, and the outlet valve closes; and
   wherein when the bubble expands, the inlet valve closes, and the outlet valve opens.

20. The method of claim 19, further comprising:
replacing the inlet valve and the outlet valve with an inlet diffuser and an outlet diffuser respectively, wherein the inlet diffuser and the outlet diffuser are conical shaped, each having a larger diameter end and a smaller diameter end, and wherein the larger diameter end of the inlet diffuser is connected to the tube, the smaller diameter end of the inlet diffuser is connected to the liquid reservoir, the smaller diameter end of the outlet diffuser is connected to the tube, and the larger diameter end of the outlet diffuser is connected to the liquid chamber.

* * * * *